(12) United States Patent
Sakuta

(10) Patent No.: US 10,989,642 B2
(45) Date of Patent: Apr. 27, 2021

(54) APPARATUS FOR AND METHOD OF MASS ANALYSIS

(71) Applicant: HITACHI HIGH-TECH SCIENCE CORPORATION, Tokyo (JP)

(72) Inventor: Masahiro Sakuta, Tokyo (JP)

(73) Assignee: HITACHI HIGH-TECH SCIENCE CORPORATION, Tokyo (JP)

(*) Notice: Subject to any disclaimer, the term of this patent is extended or adjusted under 35 U.S.C. 154(b) by 381 days.

(21) Appl. No.: 16/041,675

(22) Filed: Jul. 20, 2018

(65) Prior Publication Data

US 2019/0025174 A1 Jan. 24, 2019

(30) Foreign Application Priority Data

Jul. 21, 2017 (JP) .............................. JP2017-142235

(51) Int. Cl.
*G01N 5/04* (2006.01)
*G01N 25/48* (2006.01)
*G01N 30/86* (2006.01)
*H01J 49/00* (2006.01)
*G01N 33/00* (2006.01)

(52) U.S. Cl.
CPC ................ *G01N 5/04* (2013.01); *G01N 25/48* (2013.01); *G01N 30/8675* (2013.01); *G01N 33/0049* (2013.01); *H01J 49/0027* (2013.01); *H01J 49/0031* (2013.01)

(58) Field of Classification Search
CPC ...................................................... G01N 25/48
See application file for complete search history.

(56) References Cited

U.S. PATENT DOCUMENTS

| 10,403,487 B2* | 9/2019 | Schwieters | ........... H01J 49/025 |
| 2006/0085141 A1* | 4/2006 | Neacsu | ............... H01J 49/0036 |
| | | | 702/23 |
| 2012/0133671 A1* | 5/2012 | Setou | .................. H01J 49/0009 |
| | | | 345/593 |
| 2015/0219606 A1* | 8/2015 | Morimoto | .......... G01N 30/7233 |
| | | | 250/282 |

FOREIGN PATENT DOCUMENTS

JP 2012037385 A 2/2004

* cited by examiner

*Primary Examiner* — Daniel S Larkin
(74) *Attorney, Agent, or Firm* — Holland & Hart LLP

(57) ABSTRACT

Disclosed is an apparatus for and a method of mass analysis in which a presence of an accessory substance which is difficult to be analyzed can be recognized visually and clearly. The apparatus for mass analysis analyzes a sample containing a substance to be measured and includes: a display unit; a memory unit storing a theoretical peak obtained by calculation with respect to a region of a mass spectrum of the substance; a matching degree calculation unit calculating a matching degree from multiple peaks that each of the mass spectrum of the sample in the region and the theoretical peak have; a matching degree displaying control unit displaying the matching degree on the display unit; and a superimposition displaying control unit displaying the mass spectrum of the sample and the theoretical peak in a superimposed way in a manner that is consistent with a mass-to-charge ratio.

8 Claims, 11 Drawing Sheets

APPARATUS FOR AND METHOD OF MASS ANALYSIS

CROSS REFERENCE TO RELATED APPLICATION

This application claims priority and the benefit of Japanese Patent Application No. 2017-142235, by SAKUTA, filed Jul. 21, 2017, which is hereby incorporated by reference in its entirety into this application.

BACKGROUND OF THE INVENTION

1. Technical Field

The present invention relates generally to an apparatus for and a method of mass analysis.

2. Description of the Related Art

Decabromodiphenyl ether (DBDE), a type of polybrominated diphenyl ether, has a high bromine content and is used as a flame retardant, but has recently become a restricted substance. Therefore, it is necessary to analyze whether DBDE is contained in a sample, such as a resin.

Since DBDE is a volatile component, it is possible to analyze DBDE by applying a conventionally known evolved gas analysis (EGA). EGA is performed by analyzing gas components, which are generated by heating the sample, with various analyzing apparatuses such as gas chromatograph and mass spectrometer.

Patent Document 1 discloses a technique of mass-analyzing tetrabromobisphenol A (TBBPA), which is a bromine-based flame retardant, and determining two peak intensity ratios for TBBPA.

DOCUMENTS OF RELATED ART (Patent Document 1) Japanese Patent No. 5502648

SUMMARY OF THE INVENTION

However, signals originating from other substances in a sample (such as other components contained in the sample) overlap as noise with a mass spectrum region of DBDE, which is a substance to be measured, and thus it is difficult to perform mass analysis of the DBDE.

Accordingly, the present invention has been made keeping in mind the above problems occurring in the related art, and an object of the present invention is to provide an apparatus for and a method of mass analysis, the apparatus and the method capable of visually and clearly recognizing a presence of a substance to be measured.

In order to accomplish the above object, the present invention provides an apparatus for mass analysis, the apparatus analyzing a sample containing a substance to be measured and including: a display unit; a memory unit storing a theoretical peak obtained by calculation with respect to a region of a mass spectrum of the substance; a matching degree calculation unit calculating a matching degree from multiple peaks that each of the mass spectrum of the sample in the region and the theoretical peak have, the matching degree representing degree of matching between the mass spectrum of the sample and theoretical peak; a matching degree displaying control unit displaying the matching degree on the display unit; and a superimposition displaying control unit displaying the mass spectrum of the sample and the theoretical peak in a superimposed way in a manner that is consistent with a mass-to-charge ratio.

The apparatus for mass analysis calculates and displays the matching degree between the mass spectrum of the sample and the theoretical peak of the substance. In addition, the mass spectrum of the sample and the theoretical peak of the substance are displayed in a superimposed manner. Accordingly, a presence of the substance can be recognized visually and clearly when mass analysis is difficult.

In addition, the matching degree between the theoretical peak and the mass spectrum of the sample is represented by using the theoretical peak such that, for example, when peak shapes of the mass spectrum are unclear due to noise, the presence of the substance can be determined reliably by the matching degree of the theoretical peak.

In the apparatus for mass analysis of the present invention, the matching degree displaying control unit may compare the matching degree and a predetermined first threshold value with each other, and display a presence of the substance on the display unit.

According to the apparatus for mass analysis, a system of the apparatus compares the matching degree and the first threshold value and displays the presence of the substance, whereby the presence of the substance can be recognized without determination of an operator. In particular, in the case where a first threshold value differs for each substance, it is necessary to have experience to determine a matching degree and a presence of each substance, but the determination can be easily performed by the system.

In the apparatus for mass analysis of the present invention, the matching degree calculation unit may sum up intensities of the mass spectrum of the sample each corresponding to a same mass-to-charge ratio of the theoretical peak to calculate a sum of the intensities, and the matching degree displaying control unit may display the sum of the intensities on the display unit.

According to the apparatus for mass analysis, the sum of the intensities of the mass spectrum of the sample each corresponding to the same mass-to-charge ratio of the theoretical peak is displayed in addition to the matching degree on the display unit, whereby information for determining the presence of the substance reliably can be provided.

In the apparatus for mass analysis of the present invention, the matching degree displaying control unit may compare the sum of the intensities and a predetermined second threshold value, and may display a reliability of the presence of the substance on the display unit.

According to the apparatus for mass analysis, the system compares the sum of the intensities and the second threshold value with each other, and displays the reliability of the presence of the substance, whereby the presence of the substance can be recognized more reliably.

In the apparatus for mass analysis of the present invention, the matching degree calculation unit may calculate the matching degree on the basis of an average value of the intensities of the mass spectrum of the sample in a predetermined range of the theoretical peak.

Mass spectrum may vary with time, and in this case, a matching degree value between the mass spectrum and the theoretical peak becomes unstable. Therefore, by calculating the matching degree on the basis of the average value of intensities of the mass spectrum of the sample in the predetermined range in a direction of the mass-to charge ratio of the theoretical peak, the presence of the substance can be determined more reliably.

In the apparatus for mass analysis of the present invention, the superimposition displaying control unit may display an intensity of the maximum peak of the theoretical peak and an intensity, which has the same mass-to-charge ratio with the maximum peak, of the mass spectrum of the sample on the display unit in a superimposed manner.

According to the apparatus for mass analysis, it is easy to compare the mass spectrum of the sample and the theoretical peak.

In the apparatus for mass analysis of the present invention, the matching degree calculation unit may calculate the matching degree by using a correlation coefficient.

A method of mass analysis of a sample containing a substance to be measured, the method including: storing a theoretical peak obtained by calculation with respect to a region of a mass spectrum of the substance; calculating a matching degree from multiple peaks that each of the mass spectrum of the sample in the region and the theoretical peak have, the matching degree representing degree of matching between the mass spectrum of the sample and theoretical peak; controlling for displaying the matching degree on a display unit; and displaying the mass spectrum of the sample and the theoretical peak on the display unit in a superimposed way in a manner that is consistent with a mass-to-charge ratio.

According to the present invention, a presence of a substance to be measured can be visually and clearly recognized.

BRIEF DESCRIPTION OF THE DRAWINGS

The above and other objects, features, and advantages of the present invention will be more clearly understood from the following detailed description taken in conjunction with the accompanying drawings, in which.

DESCRIPTION OF THE PREFERRED EMBODIMENTS

Figure 1:
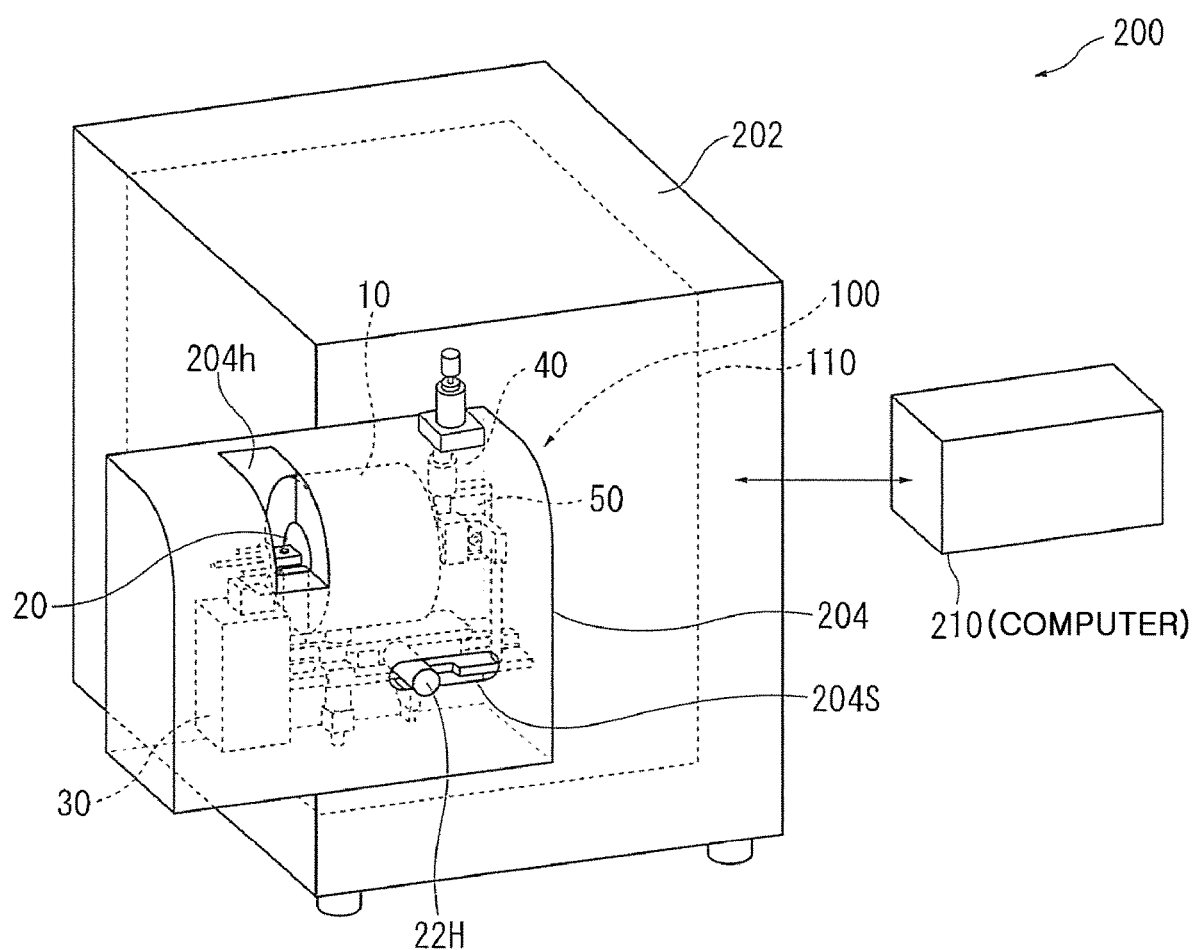
FIG. 1 is a perspective view showing a configuration of an evolved gas analyzer, which includes an apparatus for mass analysis related to an embodiment of the present invention.
Figure 2:
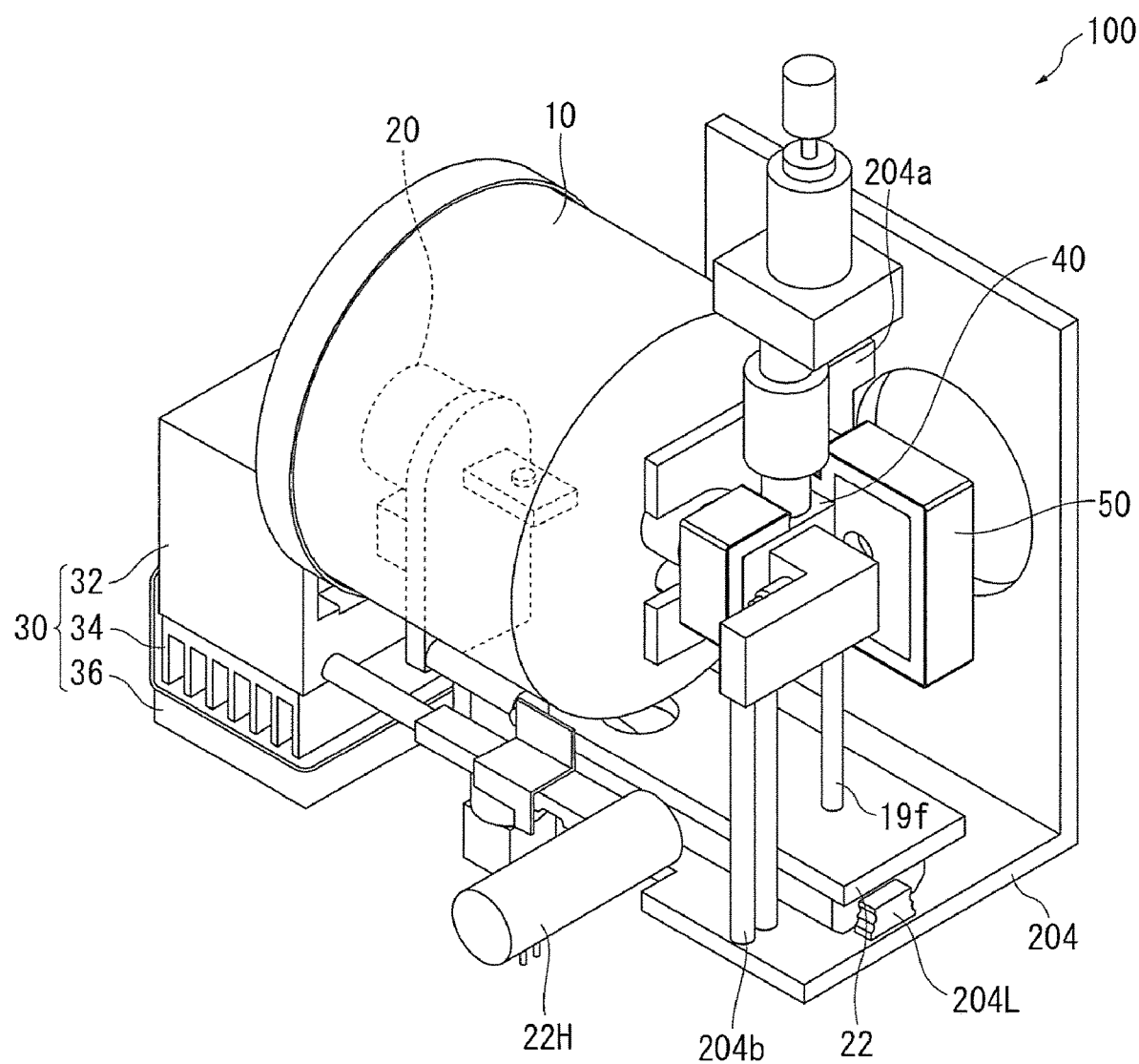
FIG. 2 is a perspective view showing a configuration of a gas evolving unit.
Figure 3:
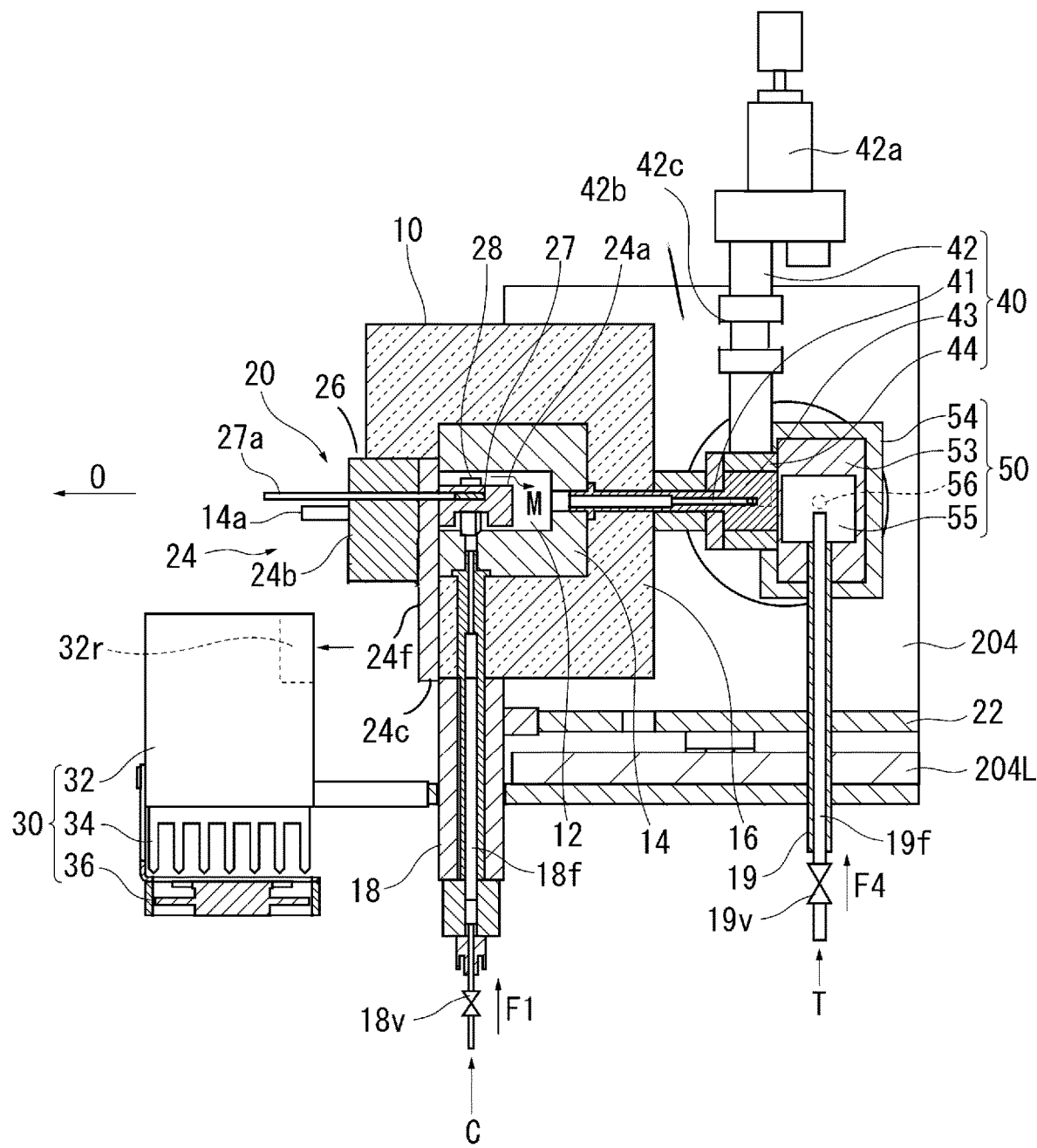
FIG. 3 is a vertical cross-sectional view showing the configuration of the gas evolving unit.
Figure 4:
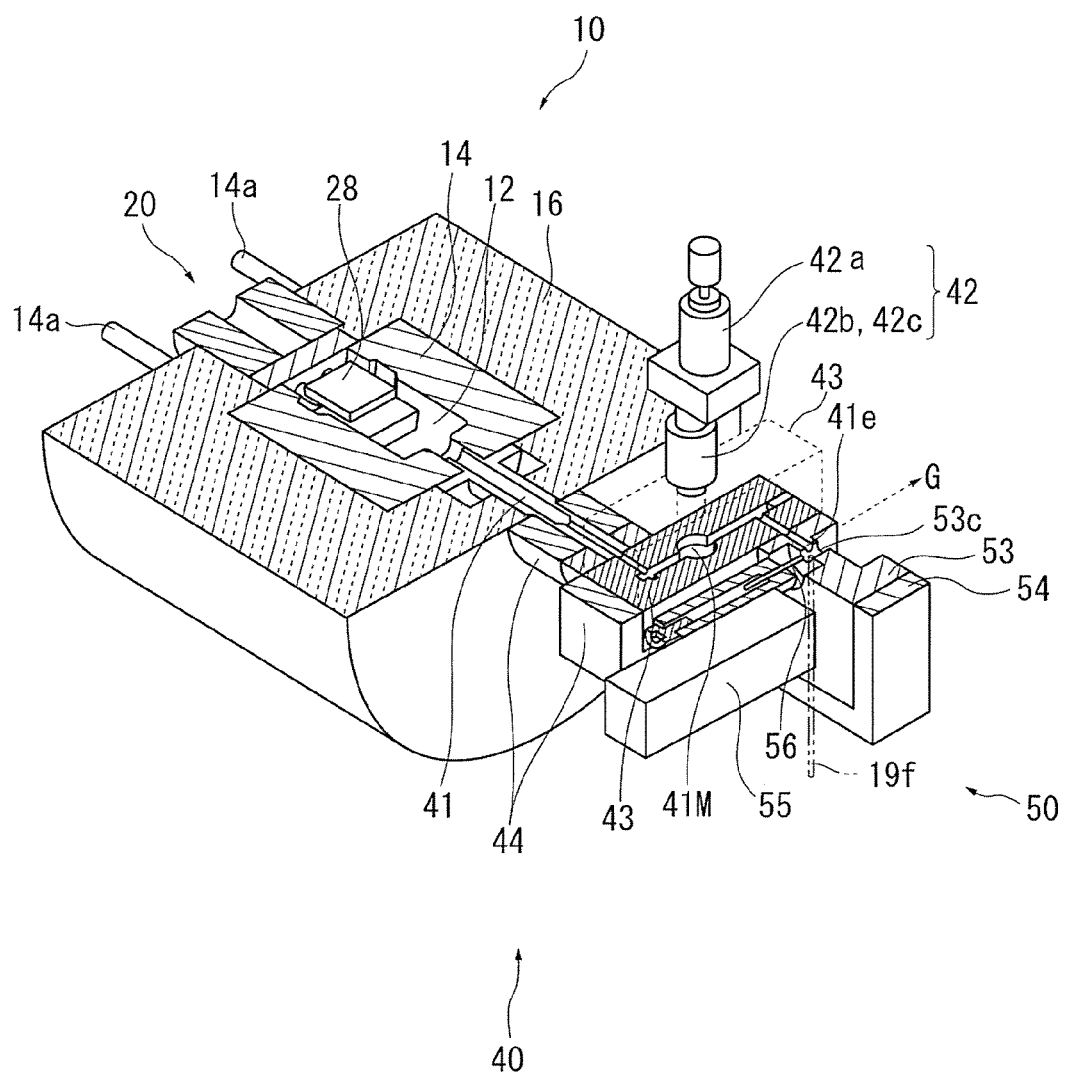
FIG. 4 is a transverse cross-sectional view showing the configuration of the gas evolving unit.
Figure 5:
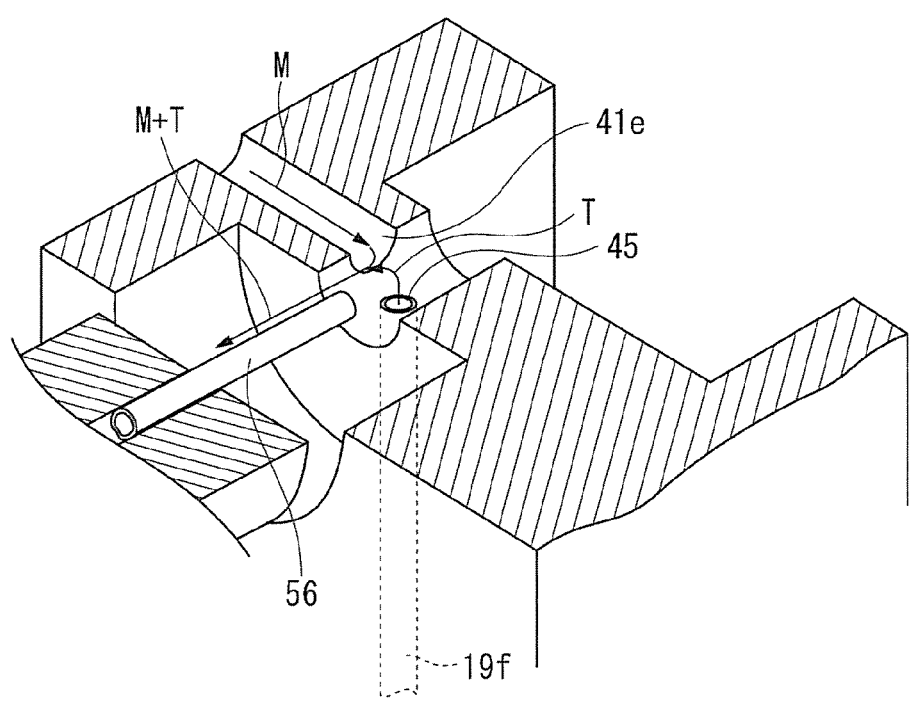
FIG. 5 is a partially enlarged view of FIG. 4.

Hereinafter, the exemplary embodiment of the present invention will be described with reference to the accompanying drawings. FIG. 1 is a perspective view showing a configuration of an evolved gas analyzer 200, which includes a mass spectrometer (apparatus for mass analysis) 110 related to an embodiment of the present invention; FIG. 2 is a perspective view showing a configuration of a gas evolving unit 100; FIG. 3 is a vertical cross-sectional view showing the configuration of the gas evolving unit 100 taken along an axis O; FIG. 4 is a cross-sectional view showing the configuration of the gas evolving unit 100 on the axis O; and FIG. 5 is a partially enlarged view of FIG. 4.

Figure 6:
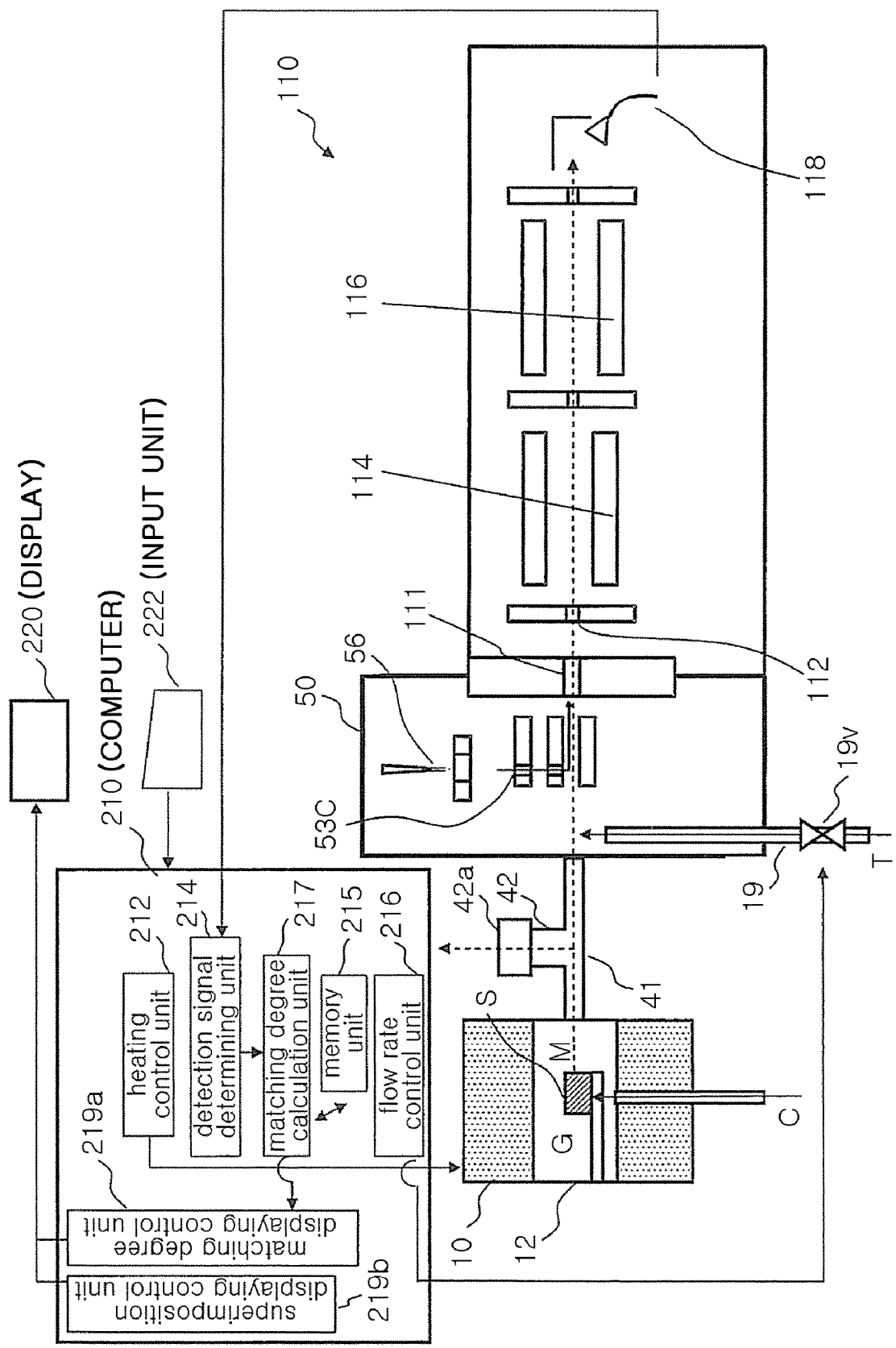
FIG. 6 is a block diagram showing a process of analyzing a gas component by the evolved gas analyzer.

The evolved gas analyzer 200 is provided with the following: a body unit 202 which is a housing; a box-shaped attaching unit 204 for a gas evolving unit, the attaching unit 204 attached to a front of the body unit 202; and a computer (control unit) 210 controlling the entire system of the evolved gas analyzer. The computer 210 is provided with a CPU processing data, a memory unit 215 storing a computer program and data, a display unit 220, such as an LCD monitor, and an input unit 222, such as a keyboard, as shown in FIG. 6.

The attaching unit 204 for the gas evolving unit stores the gas evolving unit 100 as an assembly therein, the gas evolving unit including a cylindrical furnace 10, a sample holder 20, a cooling unit 30, a splitter 40 splitting gas, an ion source 50, and an inert gas flow path 19f. In addition, the body unit 202 stores the mass spectrometer 110, as shown in FIG. 6, analyzing gas components evolved by heating a sample.

As shown in FIG. 1, the attaching unit 204 for the gas evolving unit is provided with an opening 204h extending from upper to front surfaces thereof. The sample holder 20 is located on the opening 204h by moving toward a discharging position (which will be described below) that is located at an outside of the furnace 10. Thus, a sample is supplied to or removed from the sample holder 20 through the opening 204h. In addition, the attaching unit 204 for the gas evolving unit is provided with a slit 204S at the front surface thereof. By horizontally moving an opening/closing handle 22H exposed to an outside through the slit 204S, the sample holder 20 is moved into or discharged from the furnace 10 such that the sample holder 20 is set at the above-described discharging position to supply or removing the sample.

In addition, for example, when the sample holder 20 is moved on a moving rail 204L (which will be described below) by a stepping motor, etc. controlled by the computer 210, the sample holder 20 may be automatically moved into and discharged from the furnace 10.

Hereinafter, each component in the configuration of the gas evolving unit 100 will be described with reference to FIGS. 2 to 6.

The furnace 10 is attached to an attaching plate 204a of the attaching unit 204 for the gas evolving unit to be parallel to the axis O. The furnace 10 includes a heating chamber 12 having an approximate cylindrical shape and being open on the basis of the axis O, a heating block 14, and a heat retaining jacket 16.

The heat retaining jacket 16 surrounds the heating block 14, and the heating block 14 surrounds the heating chamber 12. The heating block 14 is made of aluminum, and is heated by electricity obtained from a pair of heating electrodes 14a extending from the furnace 10 to outside in a direction of the axis O as shown in FIG. 4.

In addition, the attaching plate 204a extends in a direction perpendicular to the axis O. The splitter 40 and the ion source 50 are attached to the furnace 10. In addition, a supporter 204b extends in a vertical direction of the attaching unit 204 for the gas evolving unit and supports the ion source 50.

The splitter 40 is connected to a second side (right side of FIG. 3) of the furnace 10, which is opposite to a first side, which is an opening side of the furnace 10. In addition, a carrier gas protecting pipe 18 is connected to a lower portion of the furnace 10, and stores a carrier gas channel 18f therein, the carrier gas channel 18f being connected to a lower surface of the heating chamber 12 and introducing carrier gas C to the heating chamber 12 therethrough. In addition, the carrier gas channel 18f is provided with a control valve 18v controlling a flow rate F1 of the carrier gas C.

Furthermore, a mixed gas channel 41 communicates with the second side (right side of FIG. 3) of the heating chamber 12 such that mixed gas M of gas component G evolved from the furnace 10 (heating chamber 12) and the carrier gas C flows in the mixed gas channel 41. A detailed description will be provided later.

Meanwhile, as shown in FIG. 3, the ion source 50 is connected to the inert gas protecting pipe 19 at a lower side thereof, and the inert gas protecting pipe 19 stores the inert gas flow path 19f through which inert gas T is introduced into the ion source 50. In addition, the inert gas flow path 19f is provided with a control valve 19v controlling a flow rate F4 of the inert gas T.

The sample holder 20 is provided with the following: a stage 22 moving on the moving rail 204L attached to an inner upper surface of the attaching unit 204 for the gas evolving unit; a bracket 24c attached on the stage 22 and extending vertically; insulators 24b and 26 attached to a front surface (left side of FIG. 3) of the bracket 24c; a sample holding unit 24a extending from the bracket 24c to the heating chamber 12 in the direction of the axis O; a sample heater 27 provided immediately below the sample holding unit 24a; and a sample plate 28 provided on an upper surface of the sample holding unit 24a and above the sample heater 27 and on which the sample is placed.

Here, the moving rail 204L extends in the direction of the axis O (horizontal direction in FIG. 3), and the sample holder 20 moves back and forth by the stage 22 in the direction of the axis O. In addition, the opening/closing handle 22H is attached to the stage 22 and extends in the direction perpendicular to the axis O.

In addition, the bracket 24c has a long rectangular shape having a semicircular upper portion. The insulator 24b has an approximately cylindrical shape and is provided at a front surface of the upper portion of the bracket 24c, and an electrode 27a of the sample heater 27 penetrates the insulator 24b and protrudes to outside the gas evolving unit. The insulator 26 has an approximately rectangular shape and is provided at the front surface of the bracket 24c and below the insulator 24b. In addition, a lower portion of the bracket 24c is not provided with the insulator 26 such that a front surface of the lower portion of the bracket 24c is uncovered to provide a contact surface 24f.

The bracket 24c has a diameter slightly larger than that of the heating chamber 12 such that the bracket 24 seals the heating chamber 12 tightly, and the heating chamber 12 stores the sample holding unit 24a therein.

In addition, a sample placed on the sample plate 28 of the heating chamber 12 is heated in the furnace 10 such that a gas component G is evolved.

The cooling unit 30 is disposed at an outside of the furnace 10 (left side of the furnace 10 in FIG. 3) to face the bracket 24c of the sample holder 20. The cooling unit 30 is provided with a cooling block 32 having a rectangular shape and having a recessed portion 32r; cooling fins 34 connected to a lower surface of the cooling block 32; and a pneumatic cooling fan 36 connected to a lower surface of the cooling fins 34 and blowing air to the cooling fins 34.

In addition, when the sample holder 20 moves in the direction of the axis O on the moving rail 204L toward a left side of FIG. 3 and comes out of the furnace 10, the contact surface 24f of the bracket 24c is positioned at and contacts with the recessed portion 32r of the cooling block 32. Accordingly, the cooling block 32 absorbs heat of the bracket 24c whereby the sample holder 20 (particularly, the sample holding unit 24a) is cooled.

As shown in FIGS. 3 and 4, the splitter 40 is provided with the above-described mixed gas channel 41 communicating with the heating chamber 12; a branching channel 42 communicating with the mixed gas channel 41 and being exposed to the outside of the gas evolving unit; a back pressure valve 42a connected to a discharge side of the branching channel 42 to control a back pressure of the mixed gas M discharged through the branching channel 42; a housing unit 43 having an end of the mixed gas channel 41 inside thereof; and a heat retaining unit 44 surrounding the housing unit 43.

In addition, a filter 42b and a flowmeter 42c is disposed between the branching channel 42 and the back pressure valve 42a in the embodiment, the filter 42b removing impurities in the mixed gas. An end of the branching channel 42 may be exposed without a valve for controlling a back pressure, such as back pressure valve 42a, etc.

As shown in FIG. 4, when viewed from the top, the mixed gas channel 41 is connected to the heating chamber 12 and extends in the direction of the axis O. Then, the mixed gas channel 41 bends in a direction perpendicular to the axis O and bends again in the direction of the axis O such that the mixed gas channel 41 reaches an end part 41e and has a crank shape. In addition, a portion of the mixed gas channel 41 that extends in the direction perpendicular to the axis O is provided with a center thereof having a enlarged diameter to define a branch chamber 41M. The branch chamber 41M extends to an upper surface of the housing unit 43 and is fitted with the branching channel 42 having a diameter slightly smaller than that of the branch chamber 41M.

The mixed gas channel 41 may have a straight line, which is connected to the heating chamber 12, extends in the direction of the axis O, and reaches to an end part 41e. Alternatively, the mixed gas channel 41 may be a curved shape, or a linear shape having a predetermined angle with the axis O, etc., depending on a positional relationship with the heating chamber 12 or with the ion source 50.

As shown in FIGS. 3 and 4, the ion source 50 is provided with an ionizer housing unit 53, an ionizer heat retaining unit 54 surrounding the ionizer housing unit 53, a discharge needle 56, and a staying unit 55 fixing the discharge needle 56. The ionizer housing unit 53 has a plate shape, and a surface thereof is parallel to the axis O and is penetrated by a small hole 53c at the center thereof. In addition, the end part 41e of the mixed gas channel 41 penetrates the ionizer housing unit 53 and faces a side wall of the small hole 53c. Meanwhile, the discharge needle 56 extends in a direction perpendicular to the axis O and faces the small hole 53c.

As shown in FIGS. 4 and 5, the inert gas flow path 19f penetrates the ionizer housing unit 53 vertically, and a front end of the inert gas flow path 19f faces a bottom surface of the small hole 53c of the ionizer housing unit 53 and provides a junction 45 joining the end part 41e of the mixed gas channel 41.

In addition, with regard to the mixed gas M introduced from the end part 41e to the junction 45, which is near the small hole 53c, the mixed gas M is mixed with the inert gas T introduced from the inert gas flow path 19f such that combined gas (M+T) flows toward the discharge needle 56 and the gas component G among the combined gas (M+T) is ionized by the discharge needle 56.

The ion source 50 is a well-known device. According to the embodiment of the present invention, atmospheric pressure chemical ionization (APCI) is applied to the ion source 50. APCI causes minimal fragmentation of the gas component G such that fragmentation peak does not occur. Therefore, it is possible to detect the measurement target without separating the gas component G by using a chromatograph, etc.

The gas component G ionized at the ion source 50, the carrier gas C, and the inert gas T are introduced to the mass spectrometer 110 and analyzed.

The ion source 50 is stored in the ionizer heat retaining unit 54.

FIG. 6 is a block diagram showing a process of analyzing a gas component by the evolved gas analyzer 200.

A sample S is heated in the heating chamber 12 of the furnace 10, and the gas component G is evolved. A heating condition (temperature rising rate, maximum temperature, etc.) of the furnace 10 is controlled by a heating control unit 212 of the computer 210.

The gas component G is mixed with the carrier gas C introduced in the heating chamber 12 to be the mixed gas M. The mixed gas M is introduced in the splitter 40 and some of the mixed gas M is discharged to outside through the branching channel 42.

A remaining mixed gas M and the inert gas T introduced from the inert gas flow path 19f are introduced to the ion source 50 as the combined gas (M+T), and the gas component G is ionized.

A detection signal determining unit 214 of the computer 210 receives a detection signal from a detector 118 (which will be described later) of the mass spectrometer 110.

A flow rate control unit 216 determines whether peak intensity of the detection signal received from the detection signal determining unit 214 is within a threshold range. When the peak intensity is out of the threshold range, the flow rate control unit 216 controls an opening ratio of the control valve 19v such that a flow rate of the mixed gas M discharged from the splitter 40 to the outside through the branching channel 42, and further, a flow rate of the mixed gas M introduced from the mixed gas channel 41 to the ion source 50 is controlled, whereby a detection accuracy mass spectrometer 110 is maintained optimally.

The mass spectrometer 110 is provided with a first aperture 111 through which the gas component G ionized at the ion source 50 is introduced; a second aperture 112 through which the gas component G flows after the first aperture 111; an ion guide 114; a quadrupole mass filter 116; and the detector 118 detecting the gas component G discharged from the quadrupole mass filter 116.

The quadrupole mass filter 116 varies an applying high frequency voltage such that mass is scanned. The quadrupole mass filter 116 generates a quadrupole electric field, and detects ions by moving the ions like a pendulum swinging within the quadrupole electric field. The quadrupole mass filter 116 serves as a mass separator passing only the gas component G within a predetermined mass range such that the detector 118 may identify and quantify the gas component G.

In addition, in the embodiment, because the inert gas T flows to the mixed gas channel 41 from a downstream of the branching channel 42, the inert gas T becomes a flow resistance which suppresses the flow rate of the mixed gas M introduced to the mass spectrometer 110 such that the inert gas T controls the flow rate of the mixed gas M discharged from the branching channel 42. In detail, as the flow rate of the inert gas T increases, the flow rate of the mixed gas M discharged from the branching channel 42 increases.

Accordingly, when a large amount of gas component is evolved and a gas concentration becomes too high, the flow rate of the mixed gas discharged from the branching channel to the outside is allowed to be increased to prevent a detection signal from exceeding a detection range of the detector, whereby the measurement can be accurate.

Hereinafter, characteristics of the present invention will be described with reference to FIGS. 7 to 11. In addition, decabromodiphenyl ether (DBDE) is called a substance to be measured.

Figure 7:
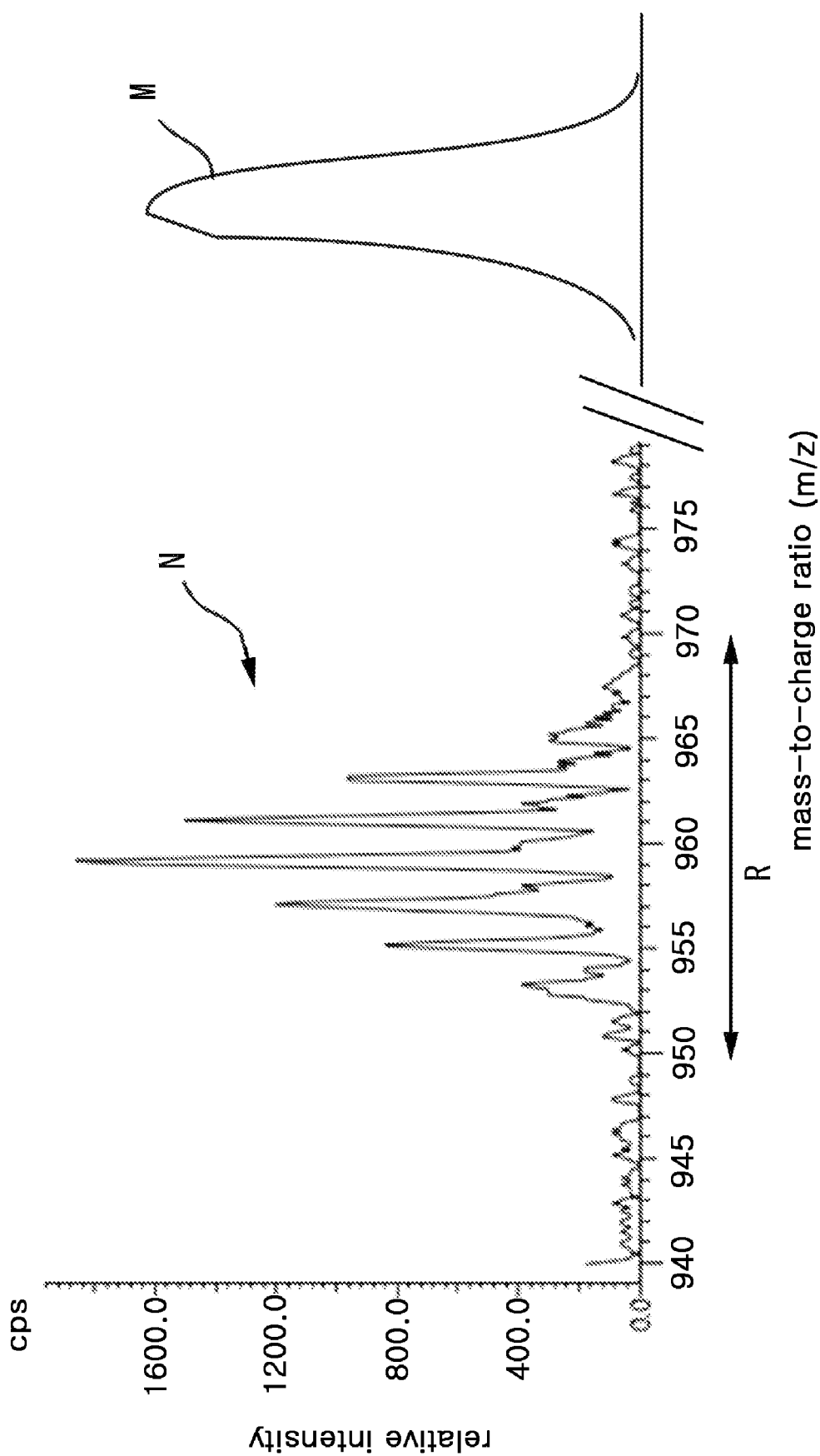
FIG. 7 is a graph showing a mass spectrum of a sample containing a substance to be measured and decabromodiphenyl ether (DBDE)

FIG. 7 is a graph showing a mass spectrum of a sample (for example, ABS resin) containing the substance. The mass spectrum of DBDE has a mass-to-charge ratio m/z in a range R between about 950 to 970. In addition, a mass spectrum M of another substance different to DBDE is out of the region R.

Figure 8:
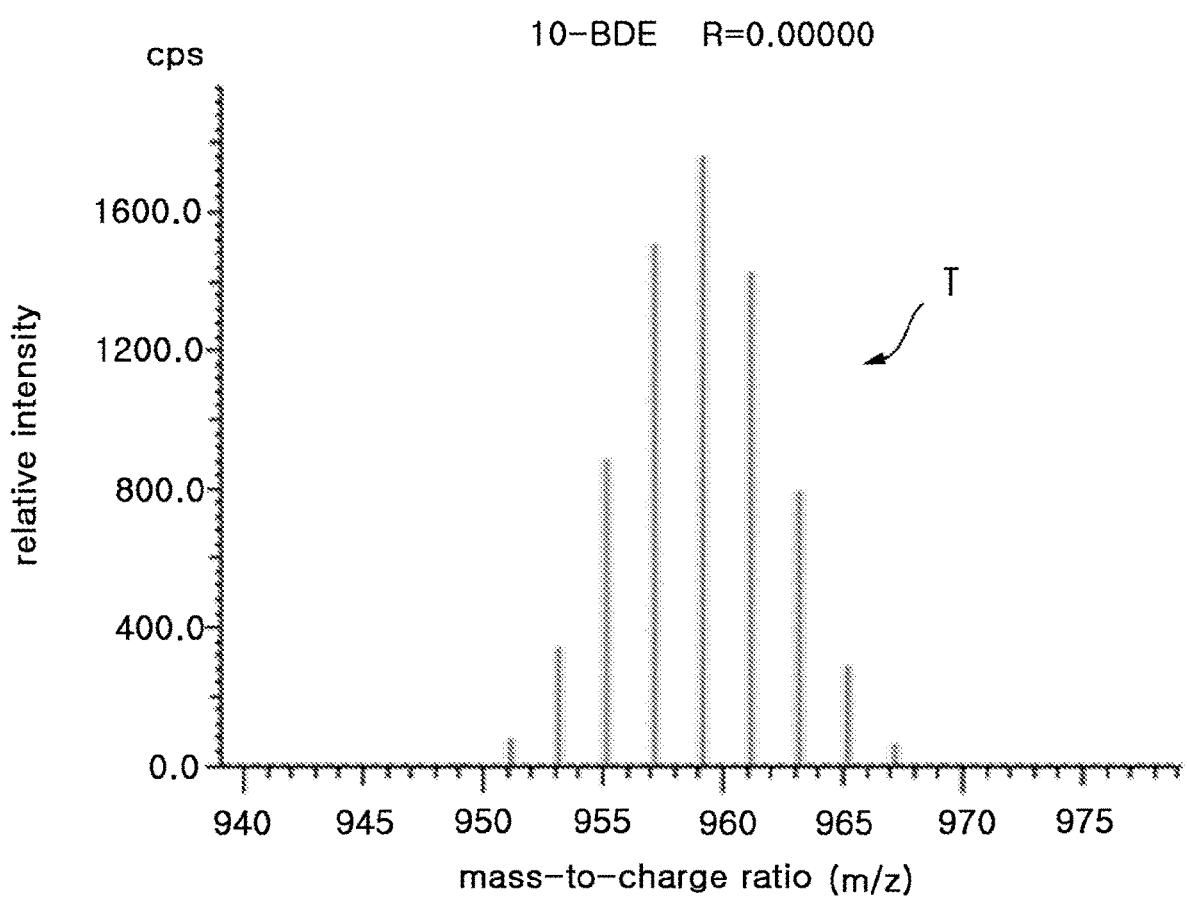
FIG. 8 is a graph showing a theoretical peak of a mass spectrum of DBDE.

FIG. 8 is a graph showing a theoretical peak T of mass spectrum of DBDE including the region R. In the exemplary embodiment, the theoretical peak T is calculated as described below. DBDE contains ten bromine atoms, and bromine has two isotopes, $^{79}$Br and $^{81}$Br, in a ratio of approximately 1:1. When one bromine molecule is present, bromine isotopes are $^{79}$Br and $^{81}$Br, and the mass spectrum represents two peaks in an intensity ratio of 1:1. When two bromine molecules are present, four cases are present, which are one case of two $^{79}$Br, two cases of one $^{79}$Br and one $^{81}$Br, and one case of two $^{81}$Br. Since there are two cases of one $^{79}$Br and one $^{81}$Br, the mass spectrum represents three peaks in an intensity ratio of 1:2:1. In this way, the theoretical peak T of a relative intensity of the peak is obtained by calculation according to binomial distribution, and DBDE has eleven peaks as shown in FIG. 8.

In addition, only nine peaks are visible in FIG. 8, but actually there are eleven peaks. The peaks at both ends on the abscissa in FIG. 8 are hardly visible because the intensity is only about 0.4% of the maximum peak. However, it is also important information that there is almost no intensity of the peaks at both ends, and the information is also used in a calculation of the following matching degree.

Figure 9:
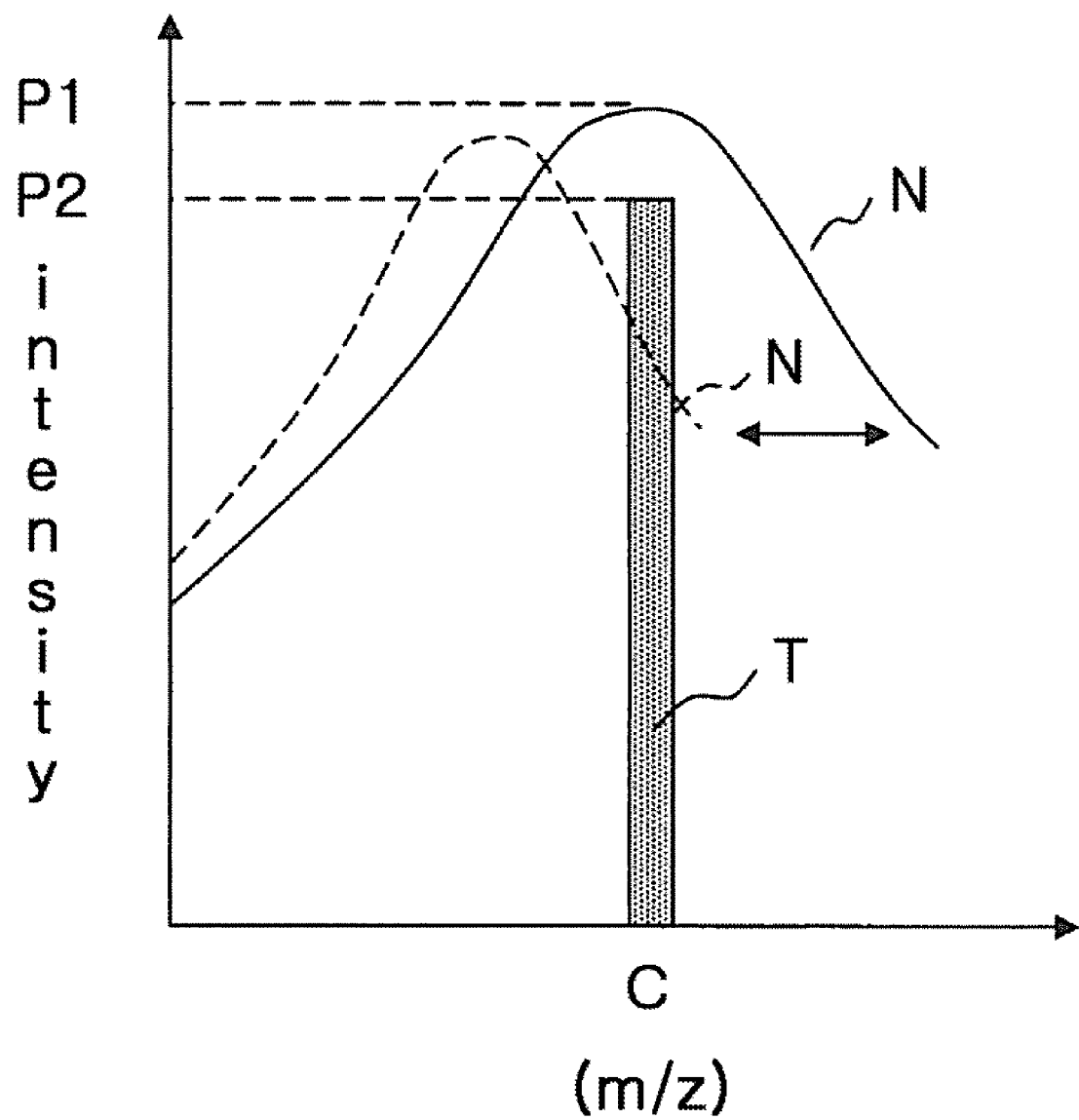
FIG. 9 is a schematic diagram showing a method of calculating a matching degree between a mass spectrum and a theoretical peak.

Then, multiple peaks that each of the mass spectrum N in the region R and the theoretical peak T has are compared with each other to calculate a matching degree indicating the degree of matching of the multiple peaks. In detail, as shown in FIG. 9, an intensity P1 of the mass spectrum N and the intensity P2 of the theoretical peak T in the same mass-to-charge ratio C are compared with each other to confirm how much P1 is similar to P2, and a correlation coefficient between P1 and P2 is calculated for each of eleven peaks constituting the theoretical peak T and the matching degree is calculated.

Specifically, let $x_i$ be the peak intensity of ith theoretical peak T, $y_i$ be the peak intensity of ith measured peak N, and n be the number of peaks, then the Pearson linear correlation coefficient R, which can be used as the matching degree, is calculated, by definition, as follows:

$$R = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$ Equation 1

In equation 1, $\bar{x}$ and $\bar{y}$ indicate averages of each variable, $x_i$ and $y_i$, respectively, that is, $$\bar{x} = \frac{1}{n}\sum_{i=1}^{n} x_i \text{ and } \bar{y} = \frac{1}{n}\sum_{i=1}^{n} y_i.$$

As a result, when the peak shape of the mass spectrum N is unclear due to noise, it is possible to determine the matching degree with characteristic portions each represented by an individual peak of the theoretical peak T such that the matching degree can be reliably calculated.

Further, as shown in broken lines in FIG. 9, the mass spectrum N may vary with time, and in this case, a matching degree value between the mass spectrum N and the theoretical peak T becomes unstable.

Figure 10:
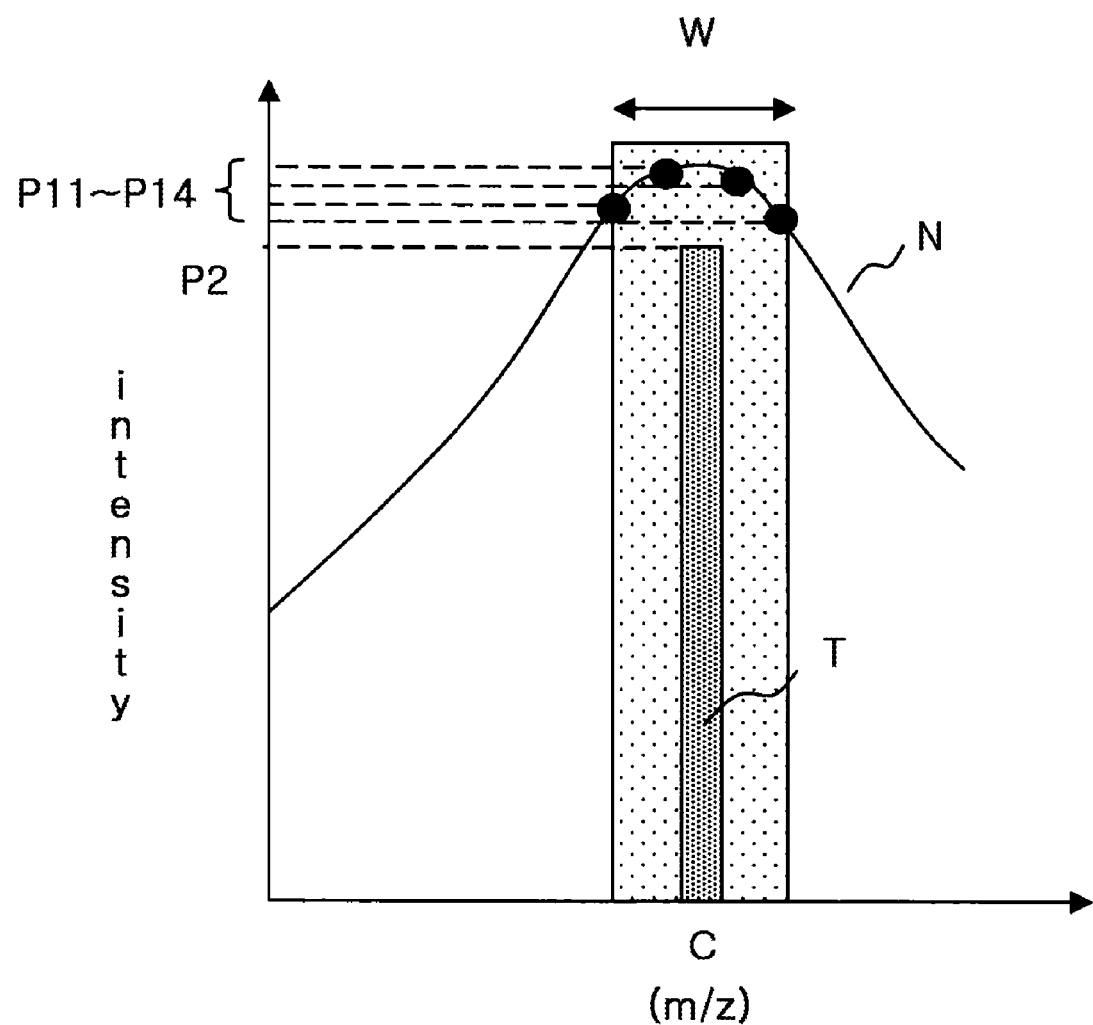
FIG. 10 is a schematic diagram showing a method of calculating a matching degree on the basis of an average value of intensities of a mass spectrum of a sample in a predetermined range of a theoretical peak.

Therefore, as shown in FIG. 10, it is preferable that the average value of the intensities of the mass spectrums N within a range of a predetermined width W in the direction of the mass-to-charge ratio of each peak of the theoretical peak T is obtained and the matching degree is calculated on the basis of the average value. In this case, intensities of each peak of the mass spectrum N is obtained as an average of mass spectrum intensities at the data points P11 through P14 (four points in FIG. 10) having slightly different mass-to-charge ratio.

Figure 11:
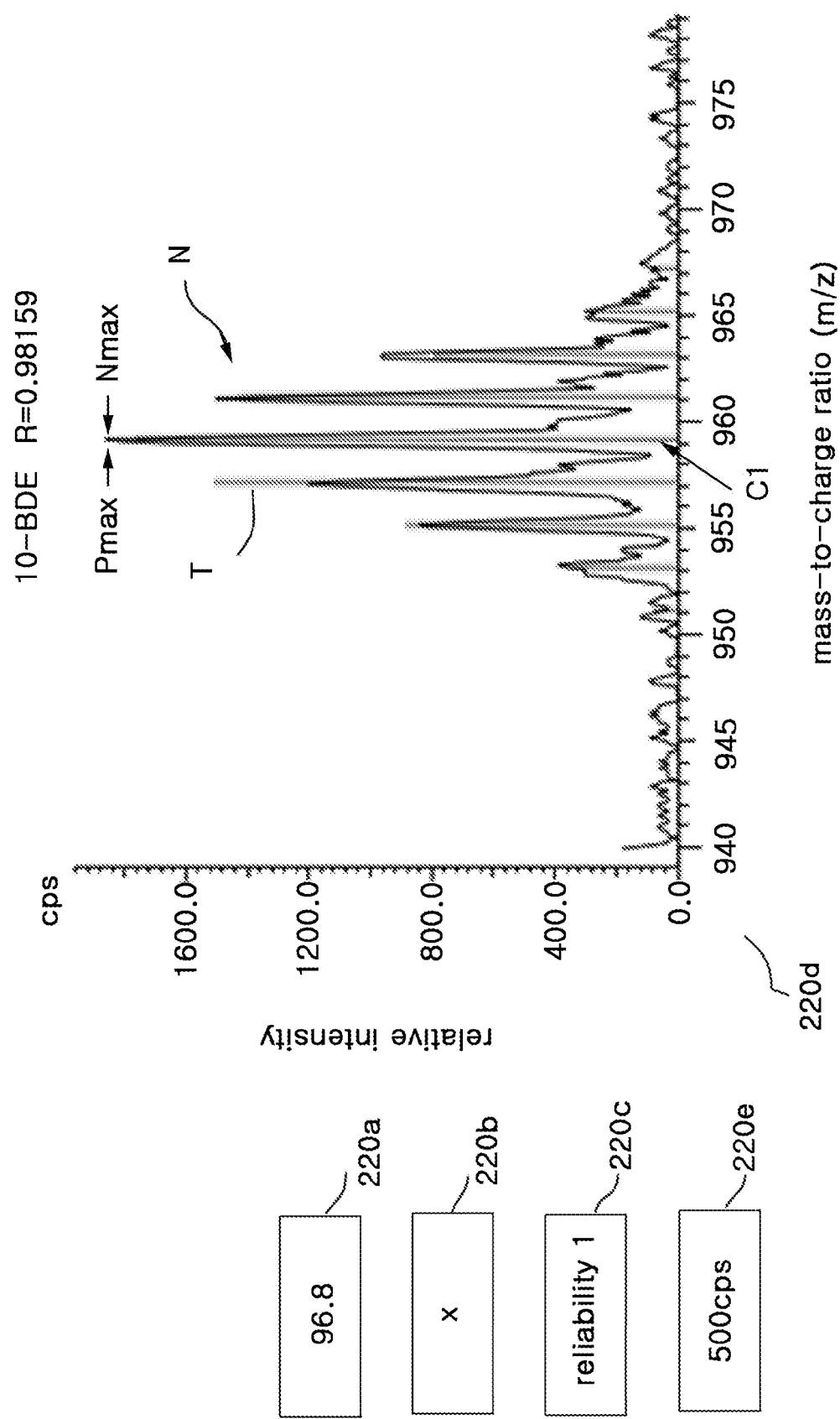
FIG. 11 is a diagram showing a mass spectrum of a sample and a theoretical peak in a superimposed way in a manner that is consistent with a mass-to-charge ratio.

Thus, as shown in FIG. 11, the matching degree (96.8% in the exemplary embodiment) is displayed on a display unit 220 (for example, a predetermined box 220a). In addition, the mass spectrum N of the sample and the theoretical peak T are superimposed on a predetermined area 220d of the display unit 220 by matching the mass-to-charge ratio.

At this point, when an intensity Pmax of the maximum peak among the theoretical peaks T and an intensity Nmax at the mass-to-charge ratio C1 equal to the maximum peak of the mass spectrum N of the sample are superimposed on each other, it is easy to compare the mass spectrum N of the sample with the theoretical peak T.

As described above, since the matching degree between the mass spectrum N of the sample and the theoretical peak T of DBDE are displayed on the display unit 220, and since the mass spectrum N and the theoretical peak T are displayed by superimposition, the presence of DBDE can be visually and clearly recognized even if the mass analysis is difficult.

In addition, since the matching degree with the mass spectrum of the sample is calculated by using the theoretical peak, even if a peak shape of the mass spectrum is not clear due to noise, the matching degree can be calculated by using the theoretical peak whereby the presence of DBDE can be reliably determined.

As shown in FIG. 11, the presence of DBDE may be displayed on the display unit 220 (for example, a predetermined box 220b) by comparing the matching degree with a predetermined first threshold value.

Since a system itself displays the presence of DBDE, the presence or absence of DBDE can be easily recognized and there is no need to determine the presence of DBDE by an operator. In particular, when first threshold values differ for each substance, it is necessary to have experience to determine each value of the matching degrees and whether the substance exists, but the determination can easily be performed by the system.

In the exemplary embodiment, the presence of DBDE is determined that when the matching degree is equal to or greater than the first threshold value and the indication is "X". This is because it is not preferable that DBDE, which is a restricted substance, is included in the sample, and the display method is not limited thereto.

Further, intensities of the mass spectrum N of the sample at the mass-to-charge ratio equal to the theoretical peak T are summed up, and the sum of the intensities may be displayed on the display unit 220 (for example, a predetermined box 220e).

At this point, a second threshold value may be set, and a reliability of the presence of DBDE may be displayed on the display unit 220 (for example, a predetermined box 220c) by comparing the sum of the intensities with the second threshold value.

In addition to the matching degree, the sum of the intensities of the mass spectrum N of the sample with respect to the mass-to-charge ratio equal to the theoretical peak T is displayed, thus providing an information that allows the operator to more reliably determine whether the theoretical peak and the mass spectrum of the sample match with each other.

Since a system itself displays the reliability for the present of DBDE, the presence or absence of DBDE can be recognized obviously. In addition, in the exemplary embodiment, when a sum of intensities is equal to or greater than a second threshold value, the system determines that the measurement is reliable and thus displays the reliability higher.

Furthermore, a method of obtaining the intensity of the mass spectrum N may only use an intensity at a mass-to-charge ratio exactly equal to the theoretical peak T. However, it is preferable to adopt an average value of intensities of the mass spectrum N within the range of the predetermined width W of the theoretical peak T and add each average value as shown in FIGS. 9 and 10.

Hereinafter, the above-described processing will be described with reference to FIG. 6.

The theoretical peak T, the first threshold value, and the second threshold value are preliminary stored in the memory unit 215, such as a hard disk. The matching degree calculation unit 217 of the computer 210 acquires the mass spectrum N of the sample in the region R in FIG. 7 from the detection signal determining unit 214, and calculates a matching degree between the mass spectrum N and the theoretical peak T. If necessary, the matching degree calculation unit 217 calculates the sum of the intensities of the mass spectrum N.

Then, a matching degree displaying control unit 219a of the computer 210 displays the obtained matching degree (and the sum of the intensities) on the display unit 220 (for example, on the respective boxes 220a and 220e), as shown in FIG. 11.

Then, a superimposition displaying control unit 219b superimposes the mass spectrum N and the theoretical peak T with respect to the mass-to-charge ratio and displays the superimposition on the display unit 220.

Preferably, the matching degree displaying control unit 219a reads the first threshold value from the memory unit 215, compares the first threshold value with the obtained matching degree, and displays the presence of DBDE on the display unit 220 (for example, the box 220b).

Preferably, the matching degree displaying control unit 219a reads the second threshold value from the memory unit 215, compares the second threshold value with the obtained the sum of the intensities, and displays the reliability of the presence of DBDE on the display unit 220 (for example, the box 220c), as shown in FIG. 11.

The present invention is not limited to the above embodiment. Accordingly, it should be understood that the present invention includes various modifications, equivalents, additions, and substitutions without departing from the scope and spirit of the invention.

A substance to be measured and a specific accessory substance are not limited to the above embodiment.

A method of calculating a theoretical peak and a method of calculating a matching degree are not limited to the above embodiment.

A method of introducing a sample into an apparatus for mass analysis is not limited to the method of evolving the gas component by thermally decomposing the sample in the furnace described above. For example, the method may be GC/MS or LC/MS of solvent extraction type in which a solvent containing a gas component is introduced and the gas component is evolved by volatilizing the solvent.

In calculating the matching degree, it is preferable to use a correlation coefficient. In particular, it is preferable to use a Pearson linear correlation coefficient.

What is claimed is:

1. An apparatus for mass analysis, the apparatus analyzing a sample containing a substance to be measured and comprising: a display unit; a memory unit storing a theoretical peak obtained by calculation with respect to a region of a mass spectrum of the substance; a matching degree calculation unit calculating a matching degree from multiple peaks that each of the mass spectrum of the sample in the region and the theoretical peak have, the matching degree representing degree of matching between the mass spectrum of the sample and theoretical peak; a matching degree displaying control unit displaying
    the matching degree on the display unit; and
    a superimposition displaying control unit displaying the mass spectrum of the sample and the theoretical peak in a superimposed way in a manner that is consistent with a mass-to-charge ratio.

2. The apparatus of claim 1, wherein the matching degree displaying control unit compares the matching degree and a predetermined first threshold value with each other, and
    displays a presence of the substance on the display unit.

3. The apparatus of claim 1, wherein the matching degree calculation unit sums up intensities of the mass spectrum of the sample each corresponding to a same mass-to-charge ratio
    of the theoretical peak to calculate a intensities, and sum of the
    the matching degree displaying control unit displays the sum of the intensities on the display unit.

4. The apparatus of claim 1, wherein the matching degree displaying control unit compares the sum of the intensities and a predetermined second threshold value, and displays a reliability of the presence of the substance on the display unit.

5. The apparatus of claim 1, wherein the matching degree calculation unit calculates the matching degree on the basis of an average value of the intensities of the mass spectrum of the sample in a predetermined range of the theoretical peak.

6. The apparatus of claim 1, wherein the superimposition displaying control unit displays an intensity of the maximum peak of the theoretical peak and an intensity, which has the same mass-to-charge ratio with the maximum peak, of the mass spectrum of the sample on the display unit in a superimposed manner.

7. The apparatus of claim 1, wherein the matching degree calculation unit calculates the matching degree by using a correlation coefficient.

8. A method of mass analysis of a sample containing a substance to be measured, the method comprising:
    storing a theoretical peak obtained by calculation with respect to a region of a mass spectrum of the substance;
    calculating a matching degree from multiple peaks that each of the mass spectrum of the sample in the region and the theoretical peak have, the matching degree representing degree of matching between the mass spectrum of the sample and theoretical peak;
    controlling for displaying the matching degree on a display unit; and
    displaying the mass spectrum of the sample and the theoretical peak on the display unit in a superimposed way in a manner that is consistent with a mass-to-charge ratio.

* * * * *